United States Patent [19]

Brandt

[11] 4,243,034
[45] Jan. 6, 1981

[54] CANNULA OR CATHETER ASSEMBLY

[75] Inventor: Werner J. Brandt, Helsingborg, Sweden

[73] Assignee: Viggo AB, Helsingborg, Sweden

[21] Appl. No.: 85,153

[22] Filed: Oct. 15, 1979

[30] Foreign Application Priority Data

Oct. 17, 1978 [SE] Sweden ................ 7810807

[51] Int. Cl.³ .............................................. A61M 5/00
[52] U.S. Cl. ................... 128/214.4; 128/221; 128/DIG. 16; 251/6
[58] Field of Search .............. 128/214.4, 221, 347, 128/218 D, 218 P, 218 NV; 251/6, 7

[56] References Cited

U.S. PATENT DOCUMENTS

| | | | |
|---|---|---|---|
| 3,197,173 | 7/1965 | Taubenheim | 251/7 X |
| 3,550,861 | 12/1970 | Teson | 251/6 X |
| 3,585,996 | 6/1971 | Reynolds | 128/214.4 |
| 4,016,879 | 4/1977 | Mellor | 128/214.4 |
| 4,121,622 | 10/1978 | Forberg | 251/6 |

*Primary Examiner*—Stephen C. Pellegrino
*Attorney, Agent, or Firm*—Beveridge, DeGrandi, Kline and Lunsford

[57] ABSTRACT

A cannula or catheter assembly has a cannula or catheter tube in a socket with a straight passageway. In order to equip such an assembly with a cheap and safe closure device which is easy to maneuvre without causing any movements injurious to the assembly, a connecting housing is fixedly or releasably connected to the socket and has a straight through-channel which is connected to the passageway of the socket and accommodates a hose section which seals against the channel wall and, to permit closing the through-channel, can be compressed at a location between its ends by means of at least one pressure body disposed in an opening in the wall of the through-channel and operable by means of a slide member movable in the axial direction of the through-channel on the outer side of the connecting housing.

5 Claims, 7 Drawing Figures

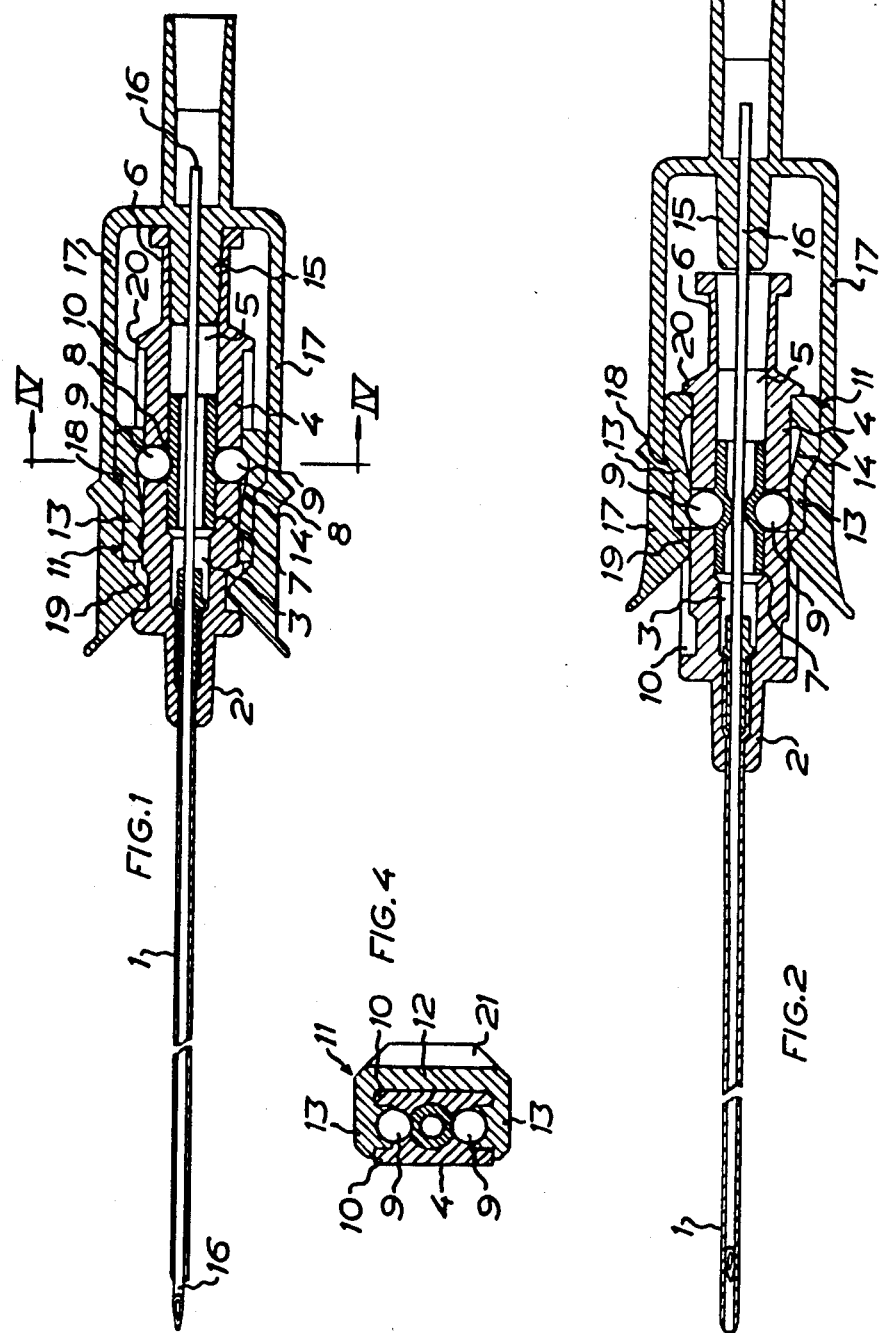

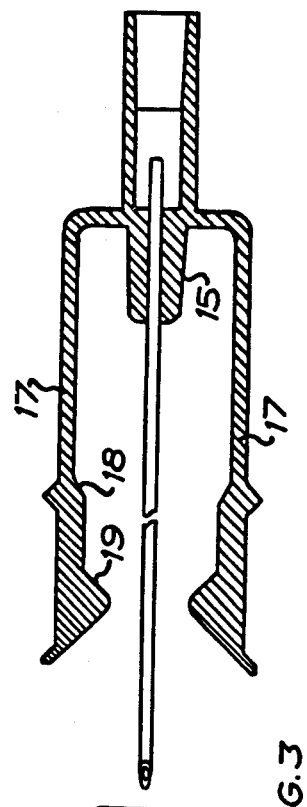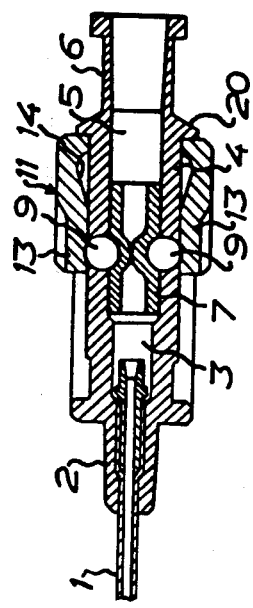
FIG. 3

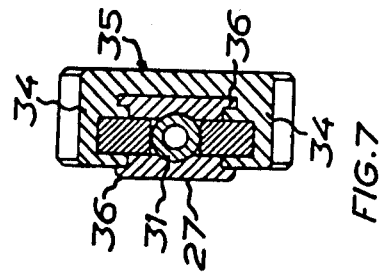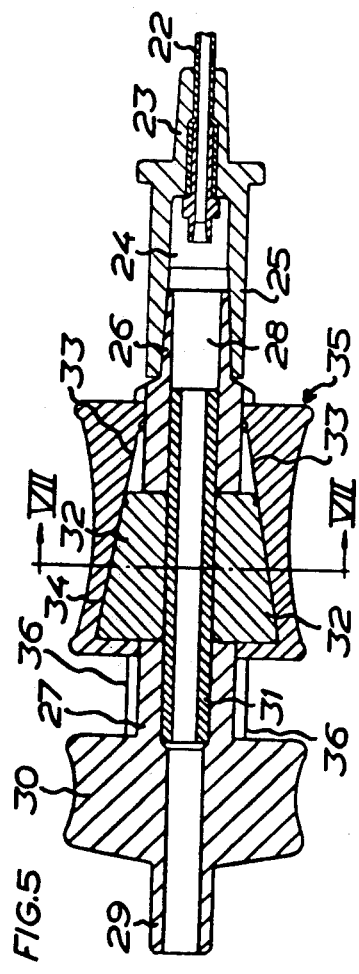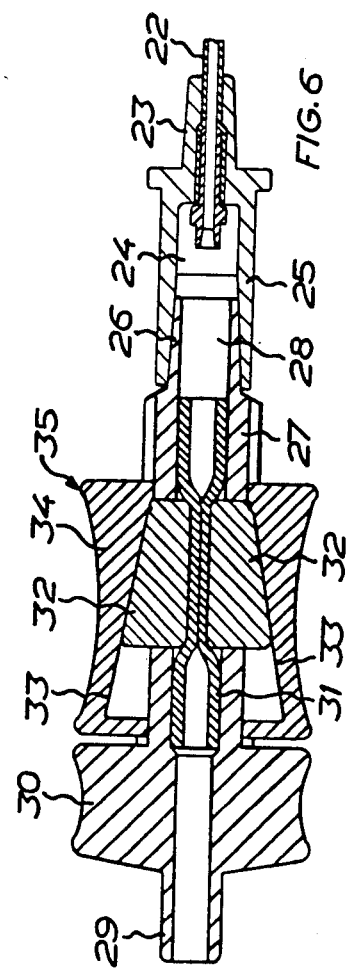

CANNULA OR CATHETER ASSEMBLY

The present invention relates to a cannula or catheter assembly having a cannula or catheter tube to be inserted in a patient, and a socket therefor which has a straight passageway to which the tube is connected.

Within many fields of application of a cannula or catheter assembly of this type, it is desirable that the assembly comprises a device for stopping or closing a flow of fluid to or from the patient through the cannula or catheter tube. Such a closure device should be of a cheap and simple construction so that the assembly may be disposed of after use. Furthermore, it must be reliable and permit rapid closure to avoid waste of fluid, and in particular to ensure that a dose administered to the patient by means of a syringe or the like can be safely determined, and to avoid that air is sucked into the patient or that parts of the equipment or the patient are smeared with fluid, for instance blood, which is difficult to remove and may give rise to bacterial growth. The closure device should also be of such a construction that, when for instance a hose or syringe is to be connected to or disconnected from the assembly, it will permit such connection and disconnection as well as the operation of the closure device without necessitating any changes of the hold or grip, such that a single person may conveniently carry out the entire operation. Similarly, it should be possible conveniently to operate the closure device without risking that the cannula or catheter tube is subjected to transverse shifting or rotation about an axis transverse to the longitudinal direction of the tube.

Prior-art assemblies of the above type equipped with closure means suffer from deficiencies in one or more of the above indicated respects and so, one aspect of the present invention is to provide a cannula or catheter assembly which meets all the requirements indicated above. To this end, the object of the invention is to provide a cannula or catheter assembly, wherein a connecting housing is formed integral with or is releasably attached to the socket and has a straight through-channel which is surrounded by a wall and is coaxial with the passageway of the socket and connected at one end to said passageway, its opposite end being provided with connecting means for coupling a hose, a syringe or the like, wherein said through-channel of the connecting housing accommodates an easily flexible hose section sealing against the channel wall, wherein the wall of the connecting housing that surrounds said channel is provided at a location between the ends of said hose section with at least one through-opening in which a pressure body is movable between one position in which said pressure body projects into said channel and maintains a portion of the hose section in a compressed closing state, and another position in which said portion of the hose section is substantially unaffected by said pressure body, and wherein a slide member mounted on the outer side of the wall surrounding said channel is movable back and forth in the longitudinal direction of the channel and has an oblique surface facing said pressure body and adapted, when said slide member is moved to displace the pressure body between said two positions.

The invention will be described in greater detail hereinbelow with reference to the accompanying drawings, in which:

FIGS. 1-3 show in axial section an infusion cannula assembly according to the invention with some mobile parts of the assembly in different positions;

FIG. 4 is a cross-section along the line IV—IV in FIG. 1;

FIGS. 5 and 6 show in axial section another embodiment of an infusion cannula assembly according to the invention with some parts of the assembly in different positions; and FIG. 7 is a cross-section along the line VII—VII in FIG. 5.

In FIGS. 1-4, there is shown an infusion cannula assembly having a cannula tube 1 which is made of an elastic flexible material and one end of which is mounted in a per se known fashion in a socket 2 made of a material, for instance polyethylene, which is relatively rigid as compared with the tube 1. The socket 2 has a straight passageway 3 to which the tube 1 is connected. The socket 2 is formed integral with a connecting housing 4 having a straight through-channel 5 which is surrounded by a wall and is coaxial with the passageway 3 of the socket and connected at one end to this passageway, its opposite end being provided with an inwardly conical connecting sleeve 6 for coupling a syringe, a hose or the like. The through-channel 5 of the connecting housing 4 accommodates an easily flexible hose section 7 sealing against the channel wall.

At a location between the ends of the hose section 7, the wall of the connecting housing 4 that surrounds the channel 5 has two diametrically opposed openings 8, each of which accommodates a pressure body 9 in the form of a spherical ball. On the outer side of the wall of the housing 4, there are provided at diametrically opposed locations guides 10 for a slide member generally designated 11 which is movable back and forth in the guides in the longitudinal direction of the channel 5. The slide member 11 is substantially U-shaped in cross-section, having a web 12 and two flanges 13. The opposed inner sides of the flanges 13 are formed with ribs engaging between the guides 10 to guide the slide member and retain it on the housing 4. The opposed sides of the ribs of the flanges 13 are formed with oblique surface 14 which abut on the pressure bodies 9 and are inclined as shown in FIGS. 1-3 with respect to the longitudinal axis of the through-channel 5.

In the embodiment of FIGS. 1-4, the cannula assembly also comprises a puncture needle unit which, as shown in FIG. 1, has a head 15 releasably mounted in the connecting sleeve 6 of the connecting housing 4, and a metal puncture cannula tube 16 projecting from the head. This puncture cannula tube is sharp-pointed at its free end remote from the head 15 and extends from the head through the through-channel 5 of the connection housing, the hose section 7 accommodated therein, the passageway 3 of the socket 2 and on through the flexible cannula tube 1 to project slightly with its spiculated end from the distal end of the flexible cannula tube with respect to the connecting housing. Two finger grip wings 17 of elastic material project from the head 15 and extend in the same direction on either side of the connecting housing 4 in the longitudinal direction thereof, the wings extending beyond and abutting on the flanges 13 of the slide member 11. As shown in FIG. 1, the wings 17 with a cam surface 18 abut on a mating cam surface on the respective slide member flange 13 and also engage an end edge of the flanges 13 with a cam surface 19.

When the infusion cannula assembly of FIGS. 1-4 is in the initial position as described above and shown in FIG. 1, the head 15 is inserted in the connecting sleeve 6 with the apex of the puncture cannula tube 16 projecting from the free end of the cannula tube 1, and the slide member 11, with respect to FIG. 1, is in a left-hand end position in which the pressure bodies 9 engage the portions of the oblique surfaces 14 of the slide member which are spaced furthest from each other, such that the pressure bodies 9 leave the hose section 7 in a practically unaffected state. The assembly may now be used in that the operator grips the wings 17 with the fingers on one hand and inserts the apex of the puncture cannula tube 16 and the free end of the cannula tube 1 in a blood vessel of a patient, whereupon the operator, with one finger of the same hand or with the other hand, firmly holds the socket 2 while the puncture needle unit is pulled to the right with respect to FIG. 1 in order entirely to remove this unit from the rest of the assembly. During the first phase of this extraction of the puncture needle unit, the cam surfaces 18 and 19 on the wings 17 will entrain the slide member 11 to the right with respect to FIG. 1 until the slide member engages an abutment or stop 20 on the connecting housing 4, as shown in FIG. 2. During this movement of the slide member 11 in the initial phase of the extraction of the puncture needle unit, the oblique surfaces 14 on the slide member 11 will urge the pressure bodies 9 into the channel 5, such that the pressure bodies sealingly press a portion of the hose 7 against the puncture cannula tube 16 while it is extracted, as appears from FIG. 2. As the extraction of the puncture needle unit proceeds from the position shown in FIG. 2, the cam surfaces 18 and 19 on the wings 17 will slide against the slide member 11 retained by the stops 20, and resiliently spread apart the wings 17 to permit continued extraction of the puncture needle unit. When the apex of the puncture cannula tube 16 during this extraction has passed beyond the pressure bodies 9, these bodies by the spring action of the flanges 13 of the slide member will be urged further into the channel 5 so as to compress a portion of the hose section 7 to an entirely closing state, as is evident from FIG. 3. The through-channel 5 of the cannula assembly thus is automatically closed as the puncture needle unit is removed, and the entire operation of extracting the puncture needle unit and closing the through-channel of the assembly can be performed with one hand or both hands without changing hold or grip, all movements being purely axial, whereby possible injurious lateral shifting or rotation of the assembly about an axis of rotation transverse to the axis of the assembly can be avoided.

If after removal of the puncture needle unit it is desirable to open the through-channel 5 of the assembly, for instance in order to introduce a liquid into the blood circulation system of the patient from a hose or syringe connected to the head or socket sleeve 15, the operator may grasp the socket 2 or the housing 4 with one hand and move the slide member 11 with one finger of the hand from the position of FIG. 3 to that of FIG. 1. The finger moving the slide member may engage either the flange 13 of the slide member or preferably its web 12, which, as shown in FIG. 4, may have one or more ribs 21 in order to improve the engagement between the finger and the slide member. Similarly, renewed closure of the through-channel 5 may be performed by moving the slide member from the position of FIG. 1 to the position of FIG. 3. When the slide member 11 is thus operated by direct finger engagement, only axial movement is needed, whereby possible injurious lateral displacement or rotation of the assembly can be avoided.

The pressure bodies 9 need not be spherical balls or other rolling bodies but may be of any other suitable design, for instance as shown in FIGS. 5-7. Further, the connecting housing need not be integral with the socket of the cannula or catheter tube but may be releasably fixed thereto. Such an embodiment is shown in FIGS. 5-7. Here, a cannula or catheter tube 22 is fixed at one end to a socket 23 with a straight passageway 24 opening in a connecting sleeve 25. A connecting piece 26 of a connecting housing 27 is inserted in the sleeve 25 and is releasably fixed to the sleeve 25 under frictional engagement or by means of a bayonet type catch (not shown). The connecting housing 27 has a straight through-channel 28 which is surrounded by a wall and is coaxial with the passageway 24 of the socket 23 and connected at one end to this passageway, while its opposite end is provided with a connecting piece 29 for coupling a hose (not shown). In the vicinity of the connecting piece 29, the housing 27 has a head 30 in the form of a finger grip member.

The through-channel 28 accommodates a hose section 31 which sealingly abuts against the channel wall. At a location between the ends of the hose section 31, the wall of the housing 27 has two diametrically opposed openings in which flat wedge-shaped pressure bodies 32 are movable between the position of FIG. 6 where the pressure bodies project into the channel 28 and maintain a portion of the hose section 31 in a compressed closing state, and the position shown in FIG. 5, in which said portion of the hose section is substantially unaffected by the pressure bodies. In order to permit such shifting of the pressure bodies 32, their outer wedge surfaces engage mating oblique surfaces 33 on the flanges 34 of a slide member generally designated 35 which is substantially U-shaped in cross-section. The connecting housing 27 has external guides 36 for guiding the slide member 35 in an axial movement with respect to the channel 28 of the connecting housing, between the position of FIG. 5 and the position of FIG. 6 for actuation of the pressure bodies 32.

By holding the head 30 with some of the fingers of one hand, it is possible to insert the cannula or catheter tube 22 in a patient and, with another finger of the same hand, to move the slide member 34, as desired, between the positions according to FIGS. 5 and 6 in order to open and close the through-channel 28 of the assembly. The movement of maneuvring the slide member 34 is purely axial, whereby possible injurious lateral displacement or rotation of the assembly can be avoided.

Although it is advisable, as shown in the drawings, to use two pressure bodies 9 and 32 diametrically opposed with respect to the hose section 7 and 31, respectively, it is possible to omit one pressure body and its associated opening in the wall of the connecting housing, it being however then necessary that the slide member be capable of moving the remaining pressure body a greater distance for closing the hose section. However, the deformation of the hose section to ensure safe closure will not be as advantageous as in the case of two pressure bodies.

What I claim and desire to secure by Letters Patent is:

1. A cannula or catheter assembly having a cannula or catheter tube (1, 22) to be inserted in a patient, and a socket (2, 23) therefor which has a straight passageway (3, 24) to which the tube is connected, wherein a connecting housing (4, 27) is formed integral with or is releasably attached to the socket (2, 23) and has a straight through-channel (5, 28) which is surrounded by a wall and is coaxial with the passageway of the socket and connected at one end to said passageway, its opposite end being provided with connecting means (6, 29) for coupling a hose, a syringe or the like, wherein said through-channel of the connecting housing accommodates an easily flexible hose section (7, 31) sealing against the channel wall, wherein the wall of the connecting housing that surrounds said channel is provided at a location between the ends of said hose section with at least one through-opening in which a pressure body (9, 32) is movable between one position at which said pressure body projects into said channel and maintains a portion of the hose section in a compressed closing state, and another position in which said portion of the hose section is substantially unaffected by said pressure body, and wherein a slide member (11, 35) mounted on the outer side of the wall surrounding said channel is movable back and forth in the longitudinal direction of the channel and has an oblique surface (14, 33) facing said pressure body and adapted, when said slide member is moved to displace the pressure body between said two positions.

2. Assembly as claimed in claim 1, wherein said oblique surface (14, 33) is arranged on a resilient portion of the slide member (11, 35) in order that the slide member be pressed elastically yieldingly against said pressure body (9, 32).

3. Assembly as claimed in claim 1 or 2, wherein the wall of the connecting housing (4, 27) that surrounds said through-channel (5, 28) has two diametrically opposed openings each accommodating a pressure body (9, 32), and wherein said slide member (11, 35) has two opposed oblique surfaces (14, 33) each of which abuts on one of said pressure bodies.

4. Assembly as claimed in claim 3, wherein said slide member (11, 35) is substantially U-shaped in cross-section, having a web and two flanges on the inner sides of which said oblique surfaces (14, 33) are arranged.

5. Assembly as claimed in claims 3 or 4, which is in the form of an infusion cannula assembly with a cannula tube (1) of flexible material and which also includes a puncture needle unit having a head (15) releasably accommodated in the connecting means (6) of said connecting housing (4) and a metal puncture cannula tube (16) which projects from said head and is sharp-pointed at its free end remote from said head and which passes from this head through said through-channel (5) of the connecting housing, said hose section (7) disposed therein, said passageway (3) of said socket and on through the flexible cannula tube to project slightly with said sharp-pointed end from the distal end of said flexible cannula tube with respect to the connecting housing, the head of the puncture needle unit being provided with two finger grip wings (17) of elastic material which extend from said head in the same direction on either side of the connecting housing in the longitudinal direction thereof, wherein the facing surfaces of said wings (17) are provided with cam surfaces (18, 19) which are adapted, as the puncture cannula tube (16) of the puncture needle unit is extracted from the infusion cannula tube (1), the socket (2) and the connecting housing (4), yieldingly to entrain the slide member (11) and displace it on said connecting housing to a position in which the pressure bodies (9) are pressed against the hose section (7).

* * * * *